United States Patent
Néron et al.

(10) Patent No.: US 8,703,486 B2
(45) Date of Patent: Apr. 22, 2014

(54) METHOD FOR POLYCLONAL IMMUNOGLOBULIN G PRODUCTION BY HUMAN B CELLS

(75) Inventors: Sonia Néron, Québec (CA); Annie Roy, Québec (CA); Jessie Farah Fecteau, San Diego, CA (US)

(73) Assignees: Université Laval, Québec (CA); Héma-Québec, Québec (CA)

( * ) Notice: Subject to any disclaimer, the term of this patent is extended or adjusted under 35 U.S.C. 154(b) by 55 days.

(21) Appl. No.: 13/120,508

(22) PCT Filed: Aug. 17, 2009

(86) PCT No.: PCT/CA2009/001150
§ 371 (c)(1),
(2), (4) Date: Sep. 12, 2011

(87) PCT Pub. No.: WO2010/034103
PCT Pub. Date: Apr. 1, 2010

(65) Prior Publication Data
US 2011/0313139 A1    Dec. 22, 2011

Related U.S. Application Data

(60) Provisional application No. 61/099,320, filed on Sep. 23, 2008.

(51) Int. Cl.
*C12N 5/06* (2006.01)
*C12N 5/08* (2006.01)
*C12N 5/00* (2006.01)

(52) U.S. Cl.
USPC .......................... 435/326; 435/373; 435/405

(58) Field of Classification Search
None
See application file for complete search history.

(56) References Cited

U.S. PATENT DOCUMENTS

| | | | |
|---|---|---|---|
| 5,817,516 A | 10/1998 | Kehry et al. | |
| 6,297,052 B1 | 10/2001 | Kehry et al. | |
| 8,153,129 B2 * | 4/2012 | Funaro et al. | 424/142.1 |
| 8,338,172 B2 | 12/2012 | Funaro et al. | |
| 2007/0098711 A1 | 5/2007 | Groen et al. | |

FOREIGN PATENT DOCUMENTS

| | | |
|---|---|---|
| EP | 0454225 | 10/1991 |
| WO | WO95/29935 | 11/1995 |
| WO | WO98/21314 | 5/1998 |
| WO | WO2010/034103 | 4/2010 |

OTHER PUBLICATIONS

Zhou et al (FASEB, 2001, v.15, p. A1217.*
Bloem et al J of Immunol., 1988, v.140, pp. 768-773.*
Purkerson et al., Eur. J. Immunol. 1991, v.21, pp. 707-714.*
Cerutti et al., J of Immunol, 1998, v.160, pp. 2145-2157.*
European Search Report corresponding to European Application No. 09815515.3-1222 / 2342350 dated May 5, 2012.
Kehry et al., "Regulation of CD40 1-15 ligand expression and use of recombinant CD40 ligand for studying B cell growth and differentiation," Seminars in Immunology (1994).
Rothermel et al., "Differential abilities of Th1 and Th2 to induce polyclonal B cell proliferation," Cellular Immunology, vol. 135, No. 1, pp. 1-15 (Jun. 1, 1991).
Etzioni, A., and Ochs, H.D., "The Hyper IgM Syndrome—An Evolving Story," Pediatric Research. vol. 56, No. 4 pp. 519-525 (2004).
Fecteau et al., "Peripheral blood CD27+ IgG+ B cells rapidly proliferate and differentiate into immunoglobulin-secreting cells after exposure to low CD154 interaction," Immunology. vol. 128 pp. e353-e365 (2008).
International Preliminary Report on Patentability corresponding to International Patent Application No. PCT/CA2009/001150 dated Dec. 1, 2010.
International Search Report corresponding to International Patent Application No. PCT/CA2009/001150 dated Nov. 25, 2009.
Néron et al., "Characterization of mononuclear cells remaining in the leukoreduction system chambers of apheresis instruments after routine platelet collection: a new source of viable human blood cells," Transfusion. vol. 47, No. 6 pp. 1042-1049 (2007).
Néron et al., "Differential responses of human B-lymphocyte subpopulations to graded levels of CD40-CD154 interaction," Immunology. vol. 116 pp. 454-463 (2005).
Tangye, S.G., and Hodgkin, P.D., "Divide the conquer: the importance of cell division in regulating B-cell responses," Immunology. vol. 112 pp. 509-520 (2004).
von Bergwelt-Baildon et al., "Human Primary and memory cytotoxic T lymphocyte responses are efficiently induced by means of CD40-activated B cells as antigen-presenting cells: potential for clinical application," Blood. vol. 99, No. 9 pp. 3319-3325 (2002).
Written Opinion of the International Searching Authority corresponding to International Patent Application No. PCT/CA2009/001150 dated Nov. 25, 2009.

(Continued)

*Primary Examiner* — Michail Belyavskyi
(74) *Attorney, Agent, or Firm* — Jenkins, Wilson, Taylor & Hunt, P.A.

(57) ABSTRACT

This application relates to an in vitro method of producing a polyclonal IgG preparation. The method comprises (i) placing a polyclonal B-cell population enriched in IgG-secreting B cells in a culture medium; and (ii) culturing the polyclonal B-cell population under conditions enabling the production of the polyclonal IgG preparation from the polyclonal B-cell population. This improved method enables the production of antibodies (preferably IgG) and facilitates long-term culture of polyclonal B-cell populations.

23 Claims, 10 Drawing Sheets

(56) References Cited

OTHER PUBLICATIONS

Fecteau, J.F., and Neron, S., "CD40 stimulation of human peripheral B lymphocytes: distinct response from naïve and memory cells," J. Immunol. vol. 171 p. 4621 (2003).

Grammer et al., "The CD40 ligand expressed by human B cells costimulates B cell responses," The Journal of Immunology. vol. 154, No. 10 pp. 4996-5010 (1995).

Néron et al., "Induction of LFA-1 independent human B cell proliferation and differentiation by binding of CD40 with its ligand," Immunol. Invest. vol. 25, Nos. 1-2 pp. 79-89 (1996).

Callard et al., "CD40 Ligand (CD40L) Expression and B Cell Function in Agammaglobulinemia with Normal or Elevated Levels of IgM (HIM). Comparison of X-Linked, Autosomal Recessive, and Non-X-Linked Forms of the Diseases, and Obligate Carriers," The Journal of Immunology. vol. 153, No. 7 pp. 3295-3306 (1994).

Deans, J.P., and Polyak, M.J., "FMC7 is an epitope of CD20," Blood. vol. 111, No. 4 p. 2492 (2008).

Demand under Article 31 PCT and Submission under Article 34 PCT corresponding to International Patent Application No. PCT/CA2009/001150 dated Jul. 16, 2010.

Funaro et al., "Generation of potent neutralizing human monoclonal antibodies against cytomegalovirus infection from immune B cells," BMC Biotechnology. vol. 8, p. 85 (10 pages) (2008).

Galibert et al., "CD40-Activated Surface IgD-Positive Lymphocytes Constitute the Long Term IL-4-Dependent Proliferating B Cell Pool," The Journal of Immunology. vol. 152 p. 22-29 (1994).

Harris, N.L., and Ronchese, F.,"The role of B-7 costimulation in T-cell immunity," Immunology and Cell Biology. vol. 77, No. 4 pp. 304-311 (1999).

Johnson-Léger et al., "Evidence for a Critical Role for IL-2 in CD40-Mediated Activation of Naive B Cells by Primary CD4 T Cells," The Journal of Immunology. vol. 161, No. 9 pp. 4618-4626 (1998).

Kindler, V., and Zubler, R.H., "Memory, but Not Naive, Peripheral Blood B Lymphocytes Differentiate into Ig-Secreting Cells After CD40 Ligation and Costimulation with IL-4 and the Differentiation Factors IL-2, IL-10, and IL-3," The Journal of Immunology. vol. 159, No. 5 pp. 2085-2090 (1997).

Klein et al., "Human Immunoglobulin (Ig)M$^+$IgD$^+$ Peripheral Blood B Cells Expressing the CD27 Cell Surface Antigen Carry Somatically Mutated Variable Region Genes: CD27 as a General Marker for Somatically Mutated (Memory) B Cells," J. Exp. Med. vol. 188, No. 9 pp. 1679-1689 (1998).

Küppers et al., "Cellular Origin of Human B-Cell Lymphomas," The New England Journal of Medicine. vol. 341, No. 20 pp. 1520-1529 (1999).

Polyak et al., "A cholesterol-dependent CD20 epitope detected by the FMC7 antibody," Leukemia. vol. 17, No. 7 pp. 1384-1389 (2003).

Wiesner et al., "Conditional Immortalization of Human B Cells by CD40 Ligation," PLoS One. vol. 3, No. 1 p. e1464 (13 pages) (2008).

* cited by examiner

METHOD FOR POLYCLONAL IMMUNOGLOBULIN G PRODUCTION BY HUMAN B CELLS

CROSS-REFERENCE TO RELATED APPLICATIONS

This application claims priority on U.S. provisional application Ser. No. 61/099,320 filed on Sep. 23, 2009, the content of which is herein incorporated in its entirety.

BACKGROUND

Nowadays, because of the lack of useful in vitro procedures, in order to obtain a polyclonal antibody preparation, one must immunize an animal (such as a rabbit, a goat, a mouse, a rat, etc.) with an antigen of interest and purify the antibodies generated from the animal. Some industries even specialize in this type of service. The resulting polyclonal antibody preparations are labor-intensive and costly.

Some systems have been developed for the large-scale in vitro production of monoclonal antibodies. One process widely used is the production of hybridomas (e.g., immortalized B-cell lines capable of secreting a specific monoclonal antibody). However, hybridomas are not necessarily stable and may lose their ability to proliferate or secrete immunoglobulins as they are cultured. Attempts have been made to produce more stable hybridomas. For example, U.S. application Ser. No. 11/509,364 (published under 2007/0098711 on May 3, 2007) describes a method for stabilizing an antibody-secreting cell by repeated oligoclonal handpicking.

Other culture systems have been developed to generate more stable B-cell cultures capable of proliferation and/or differentiation. One of these systems is the CD40L or CD154 system. For example, U.S. Pat. No. 5,817,516 (granted on Oct. 6, 1998) and U.S. Pat. No. 6,297,052 (granted on Oct. 2, 2001) describe the use of CD40L to facilitate the proliferation and the differentiation of B cells cultured in vitro. However, the isotypes of immunoglobulins (Ig) harvested under the conditions described in U.S. Pat. No. 5,817,516 or 6,297,052 are not similar to those observed in peripheral blood, suggesting that these methods introduce bias in the secretion of Ig.

The CD40-CD154 culture system is a model of the in vivo interaction between CD40 present on B cells and CD154 present on activated T cells[1]. The utility of this model has been demonstrated by Banchereau et al. in 1991, as it allows to grow human B cells in culture independently of classical mitogens and/or antigenic stimulation and to prepare human immunoglobulins and monoclonal antibodies[2]. At that time, Banchereau used B cells isolated from human tonsils[3]. Since then, many other investigators have used this culture system as a means of activating human B cells from other sources, such as the spleen[4] and blood[5-7], to study their physiological characteristics in relation to the immune response. Most groups have been sorting B cells on the basis of the expression of CD27 molecules on the cell surface, CD27+ cells being recognized as memory B cells, and CD27- cells as naïve B cells, respectively involved in secondary and primary immune responses.

It would be highly desirable to be provided with an in vitro method for the production of a large quantity of immunoglobulin G. This method should enable the proliferation and the differentiation of IgG-secreting B cells. Preferably, this method should allow the large-scale production of human IgGs.

BRIEF SUMMARY

The present invention relates to the in vitro cell culture of B cells. The methods presented herewith not only enable the production of an in vitro polyclonal IgG preparation but also enables the rapid expansion of the cultured B cells.

According to a first aspect, the present application provides an in vitro method for producing a human polyclonal IgG preparation. This method comprises placing a human polyclonal B-cell population enriched in IgG-secreting B cells in a culture medium; and culturing the human polyclonal B-cell population under conditions enabling the production of the human polyclonal IgG preparation from the polyclonal B cell population. In an embodiment of this method, the original human polyclonal B-cell population has a concentration of IgM-secreting cells of less than 5%, less than 4%, less than 3%, less than 2%, less than 1%, less than 0.5%, less than 0.4%, less than 0.3%, less than 0.2% and/or less than 0.1%. In another embodiment, the original human polyclonal B-cell population has a concentration of IgD-secreting cells of less than 5% and/or less than 1%. In another embodiment, the original human polyclonal B-cell population has a concentration of IgG-secreting cells of more than 40%, more than 50%, more than 60%, more than 70%, more than 80%, more than 90%, more than 95% and/or more than 99%. In still another embodiment, the human polyclonal B-cell population further comprises IgA-secreting cells and/or IgE-secreting cells. In yet another embodiment, the human polyclonal B-cell population is derived from peripheral blood. In still another embodiment, the human polyclonal IgG preparation comprises at least one of the following gamma isotypes of IgG antibodies: $IgG_1$, $IgG_2$, $IgG_3$ and $IgG_4$. In a further embodiment, the human polyclonal IgG preparation comprises all the following gamma isotypes of IgG antibodies: $IgG_1$, $IgG_2$, $IgG_3$ and $IgG_4$. In still a further embodiment, the relative proportions of IgG isotypes in the human polyclonal IgG preparation are similar to the relative proportions of IgG isotypes in human blood. In a further embodiment, the concentration of IgG in the human polyclonal IgG preparation is more than 70% of the total Ig content, more than 80% of the total Ig content, more than 85% of the total Ig content, more than 90% of the total Ig content, more than 95% of the total Ig content and/or more than 99% of the total Ig content. In still another embodiment, the concentration of IgM in the human polyclonal IgG preparation is less than 10% of the total Ig content, less than 9% of the total Ig content, less than 8% of the total Ig content, less than 7% of the total Ig content, less than 6% of the total Ig content, less than 5% of the total Ig content, less than 4% of the total Ig content, less than 3% of the total Ig content, less than 2% of the total Ig content, less than 1% of the total Ig content and/or less than 0.5% of the total Ig content. In a further embodiment, the concentration of the human polyclonal IgG preparation in the culture medium supernatant is more than 10 μg/mL, more than 15 μg/mL and/or more than 20 μg/mL. In still another embodiment, the human polyclonal B-cell population has been cultured for more than 30 days, more than 40 days, more than 50 days and/or more than 60 days. In another embodiment, the IgM secretion rate in the human polyclonal IgG preparation is equal to or less than 1000 ng per $10^6$ B cells per day. In a further embodiment, the method further comprises depleting the polyclonal B-cell population from IgM-secreting cells. In yet another embodiment, the method further comprises depleting the polyclonal B-cell population from IgD-secreting cells. In still another embodiment, the method further comprises harvesting the human polyclonal IgG preparation from the culture medium supernatant. In yet a further embodiment, the culture medium comprises at least one of the following: interleukin(IL)-2, IL-4 and IL-10.

According to a second aspect, the present application also provides an in vitro method of expanding a human polyclonal B-cell population. The method comprises enriching a human polyclonal B-cell population in IgG-secreting cells to provide a human polyclonal B-cell population enriched in IgG-secreting cells, placing the human polyclonal B-cell population enriched in IgG-secreting cells in a culture medium; and culturing the human polyclonal B-cell population enriched in IgG-secreting cells under conditions enabling the multiplication of the polyclonal B-cell population. Various embodiments of the concentration of IgM-secreting cells, IgD-secreting cells and IgG-secreting cells in the original human B-cell population have been described above and can be applied in this method. In an embodiment, the human polyclonal B-cell population can also further comprise IgA-secreting cells and/or IgE-secreting cells. In an embodiment, the human polyclonal B-cell population is derived from peripheral blood. In yet another embodiment, the relative proportions of IgG isotype-secreting cells in the human polyclonal IgG preparation is similar to the relative proportions of IgG isotype-secreting cells in human blood. Various embodiments of the length of the culture of the human polyclonal B-cell population have been described above and can be applied in this method. In an embodiment, the method can further comprise depleting the human polyclonal B-cell population from IgM-secreting B cells and/or IgD-secreting B cells. In another embodiment, the culture medium comprises at least one of the following: interleukin(IL)-2, IL-4 and IL-10.

According to a third aspect, the present application provides a human polyclonal IgG preparation prepared by the method described herein.

According to a fourth aspect, the present application provides a human polyclonal B-cell population prepared by the method described herein.

BRIEF DESCRIPTION OF THE DRAWINGS

Having thus generally described the nature of the invention, reference will now be made to the accompanying drawings, showing by way of illustration, a preferred embodiment thereof, and in which:

FIG. 1. IgG+ B cells expand in response to a high level of CD40-CD154 interaction. (A) Ten samples of IgG+-enriched B cells were cultured for 35 to 65 days in the presence of IL-2, IL-4 and IL-10 and CD154+ feeder cells (L4.5 cell line) at a ratio of five B cells per L4.5 cell. Expansion factors for the ten independent samples are plotted as a function of time (days) in culture. (B) Regression analysis of the ten exponential growth curves presented in (A). The correlation coefficient is 0.9965 and the equation is y=10 (0.1344x+0.5415). (C) The proportion of viable cells during long-term culture was determined on the indicated days for the ten independent samples based on Trypan blue dye exclusion and cell counts with a hemacytometer. (D) The average and standard deviation of viability (%) of the ten samples is plotted as a function of time.

FIG. 2. IgG+ cells secrete high levels of polyclonal IgG representing the four gamma isotypes in relative proportions similar to those of human blood. (A) Secretion rates were determined for each gamma isotype 1, 2, 3 and 4 between days 28 and 37 of culture for enriched IgG+ B cells in the ten independent samples described in FIG. 1. Cells were harvested and washed before being seeded again in the absence of cytokines and L4.5 cells, and were further incubated for 22 hours before IgG measurements by ELISA. Average secretion rates with error bars are shown in ng per $10^6$ cells per 24 hours for the ten independent cultures tested. (B) The polyclonality of total IgGs present in supernatants from a representative culture of IgG+-enriched B cells (c.f. FIG. 1) was analyzed by isoelectric focusing (IEF) as a function of time. From left to right, lanes correspond to an IEF standard, a commercial preparation of human intravenous immunoglobulin, an unrelated human monoclonal IgG, and culture supernatants sampled on day 16, 21, 30, 41 and 49, respectively, from IgG+ B cells cultured in the presence of IL-2, IL-4 and IL-10 and L4.5 cells. This pattern is representative of the ten independent cultures presented in FIG. 1.

FIG. 3. IL-4 and IL-10±IL-2 induce high proliferation and secretion. A sample of IgG+-enriched B cells was cultured for 53 days in the presence of IL-4 and IL-10, with or without IL-2, using the same B-cell to L4.5-cell ratio as in FIG. 1A. (A) Expansion factors are plotted as a function of time (days) in culture. (B) In these two culture conditions, IgG secretion rates for the four γ-isotypes were determined on day 37 over a 22 hour-period, as described in FIG. 2A.

FIG. 4. Cells can be expanded in larger volumes during long-term culture. (A) Three IgG+-enriched B-cell samples were cultured as described in FIG. 1 in Petri dishes to test the feasibility of increasing the culture volume up to 400-500 mL. "Real" culture volumes are shown as a function of time. Expansion factors in Petri dishes were similar to those obtained in 6-well plates performed in parallel for each sample. (B) IgA, IgG and IgM concentrations were determined in supernatants of the three independent samples described in (A) at the end of the culture. IgM content was lower than 3% of total Ig, IgA could reach up to 30% of total Ig, and IgG represented 70 to 92% of the total secreted Ig. Secretion rates and IEF patterns for these three cultures were similar to those of cultures presented in FIGS. 2A and 2B, respectively.

DETAILED DESCRIPTION

In accordance with the present invention, there is provided an improved method for producing a human polyclonal IgG preparation. This method is particularly advantageous because it enables the long-term culture of a polyclonal B cell population and does not induce bias in the secretion of IgG isotypes. Moreover, the polyclonal preparation obtained possesses all IgG gamma isotypes present in relative proportions similar to those of human blood. As it is currently known in the art, in human blood, the relative proportions of the four IgG isotypes are: $IgG_1 > IgG_2 > IgG_3 > IgG_4$.

The recent optimization of culture conditions allowed the sustained proliferation and differentiation of human B lymphocytes into IgG-secreting cells, with the ultimate goal of improving the production of a human polyclonal IgG preparation. The applicant has observed that the growth and maintenance of a high proportion of memory IgG+ cells require an extensive depletion of B cells expressing IgM and IgD. The applicant hereby presents experimental results demonstrating that depletion of IgM+ and IgD+ cells from the initial B-cell population enables the long-term growth of IgG+ B cells accompanied by a high IgG secretion rate, thereby improving the production of a human polyclonal IgG preparation.

The present application thus relates to an in vitro method for the production of a polyclonal IgG preparation. The method essentially comprises in placing a polyclonal human B-cell population enriched in IgG-secreting cells in a culture medium; and culturing the polyclonal B-cell population under conditions enabling the production of the polyclonal IgG preparation from the polyclonal B-cell population.

As used herein, the term "B cell" refers to lymphocytes that play a role in the humoral immune response and is a component of the adaptive immune system. In this application the expressions "B cell", "B-cell" and "B lymphocyte" refer to the same cell. B cells can be isolated from a primary explant containing B cells or from an extract. B cells are usually isolated from the spleen, tonsils, bone marrow or peripheral blood of mammals. In an embodiment, the subject has been previously put in contact with a specific antigen or epitope and has produced B-cell clones specific to that antigen or epitope. The present method also contemplates the use of B cells directly isolated from a subject (e.g. such as "raw" extracts) or cultures of B cells derived from such isolates.

B cells can be obtained from various sources, for example, human or other primate, rodent (including a rat or a mouse), horse, cow, dog, cat, pig, goat, sheep, llama, camel, dromedary, or rabbit. Alternately, B cells can be obtained from an avian source, such as a chicken, turkey, duck or goose. B cells could also be derived from a reptile such as a snake, crocodile or turtle, or a fish such as a carp or a shark. In an embodiment, B cells are initially exposed to an antigen or pathogen of interest prior to their incorporation in the method presented herein. In some embodiments, B cells are derived from a subject afflicted with a cancer or who has received a vaccination intended to mount an antibody response against a tumor or tumor-associated antigen. In another embodiment, the subject is afflicted with an autoimmune disease or has mounted an antibody response to an autologous antigen such as autologous tissues or factors such as coagulation factors or cytokines. In yet another embodiment, the subject is afflicted with an allogeneic condition or has mounted an antibody response to an allogeneic tissue or factors such as the Rhesus D antigen. In still another embodiment, the subject has been exposed to an antigen or a pathogen of interest.

Immature B cells are produced in the bone marrow of most mammals. After reaching the IgM+ immature stage in the bone marrow, these immature B cells migrate to lymphoid organs, where they are referred to as transitional B cells, some of which subsequently differentiating into mature B lymphocytes. B-cell development occurs through several stages, each stage characterized by a change in the genome content at the antibody loci.

Each B cell has a unique receptor protein (referred to as the B-cell receptor (BCR)) on its surface that is able to bind to a unique antigen. The BCR is a membrane-bound immunoglobulin, and it is this molecule that allows to distinguish B cells from other types of lymphocytes, as well as playing a central role in B-cell activation in vivo. Once a B cell encounters its cognate antigen and receives an additional signal from a T helper cell, it can further differentiate into one of two types of B cells (plasma B cells and memory B cells). The B cell may either become one of these cell types directly or it may undergo an intermediate differentiation step, the germinal center reaction, during which the B cell hypermutates the variable region of its immunoglobulin gene ("somatic hypermutation") and possibly undergoes class switching.

Plasma B cells (also known as plasma cells) are large B cells that have been exposed to an antigen and are producing and secreting large amounts of antibodies. These are short-lived cells and usually undergo apoptosis when the agent that induced the immune response is eliminated.

Memory B cells are formed from activated B cells that are specific to an antigen encountered during a primary immune response. These cells are able to live for a long time, and can respond quickly following a second exposure to the same antigen.

As used herein, the term "antigen" refers to an agent to which an antibody can bind to via its antigen-binding sites. Antigens come in various forms and include, but are not limited to, proteins, peptides, carbohydrates, lipids, synthetic compounds and combinations thereof. An antigen comprises one or more than one epitope. An epitope, also known as an antigenic determinant, is the part of an antigen that is recognized by the immune system.

As used herein, the term "culturing" or "cultured" refers to the in vitro steps necessary to incubate a population of cells (such as a polyclonal B-cell population) under conditions that support the growth, viability and/or differentiation of the cells. In the art, it is widely recognized that a number of formats, medias, temperature ranges, gas concentrations, culture additives, will support the growth, viability and/or differentiation of the cells, and that specific parameters need to be defined in the culture system of interest. The parameters of the culture will vary depending on the format selected and the specific goals of the culture (e.g., the production of a polyclonal IgG preparation). It is recognized that the determination of adequate culture parameters is routine in the art. In the methods described herein, the parameters must be optimized for the production of a large quantity of IgGs.

To determine if the culture conditions are adequate, one can monitor various parameters of cultured B cells. In order to determine the proliferation of B cells during culture, a variety of procedures are currently known and used in the art. These methods include, but are not limited to, the measure of incorporation of a labeled compound (such as tritiated thymidine, bromodeoxyuridine), direct cell counts, fluorometry-derived counts, PCR, etc. In order to determine the differentiation of B cells and their ability to produce immunoglobulins, procedures currently known and used in the art exists. These procedures include, but are not limited to, flow cytometry, ELISA and PCR.

As used herein, the term "polyclonal B-cell population" refers to a population of B cells that contains more than one B cell clone. As it is currently known in the art, B cells exist as clones, e.g., each B cell is derived from a unique precursor, and thus, the antibodies that their differentiated progenies produce can recognize and/or bind to a unique epitope. The method contemplates the use of B cells in a polyclonal B-cell population that are derived from various sources such as primary B cells and immortalized B cells.

As indicated above, the enrichment of IgG-expressing cells within the B-cell population allows the production of an important quantity of antibodies and enables the long-term culture of B cells. The polyclonal B-cell population that can be used in the present method comprises more than one IgG-secreting B-cell clone, more than two IgG-secreting B-cell clones or more than three IgG-secreting B-cell clones. In an embodiment, the polyclonal B-cell population comprises mostly IgG-secreting B cells (or B-cell clones). In another embodiment, the polyclonal B-cell population comprises almost exclusively IgG-secreting cells or clones. In yet a further embodiment, the polyclonal B-cell population has a concentration of IgG-secreting cells of more than 40%, more than 50%, more than 60%, more than 70%, more than 80%, more than 90%, more than 95% or more than 99%. In a further embodiment, the polyclonal B-cell population has a concentration of IgG-secreting cells of between 40% and 90%, between 40% and 95%, between 40% and 99%, between 90% and 95%, between 90% and 99% and/or between 95% and 99%.

In yet another embodiment, the polyclonal B-cell population that is put in culture is substantially devoid of IgD-secreting cells. In another embodiment, the polyclonal B-cell population that is originally submitted to culture has relatively low levels of IgD-secreting cells. In yet another embodiment, the concentration of IgD-secreting B cells in the polyclonal B-cell population is less than 5% or less than 1%.

Alternatively, the concentration of IgD-secreting B cells in the polyclonal B-cell population is between 5% and 1%.

In still another embodiment, the polyclonal B-cell population that is put in culture is substantially devoid of IgM-secreting cells. In another embodiment, the polyclonal B-cell population that is originally submitted to culture has relatively low levels of IgM-secreting cells. In yet another embodiment, the concentration of IgM-secreting B cells in the polyclonal B-cell population is less than 5% or less than 1%. Alternatively, the concentration of IgM-secreting B cells in the polyclonal B-cell population is between 5% and 1% or 1% and 0.1%.

In yet another embodiment, the polyclonal B-cell population that is put in culture is substantially devoid of both IgD- and IgM-secreting cells. In another embodiment, the polyclonal B-cell population that is originally submitted to culture has relatively low levels of both IgD- and IgM-secreting cells. Embodiments of these low levels have been suggested above.

In another embodiment, the polyclonal B-cell population also comprises other cells known in the art to be present in such polyclonal populations. For example, the polyclonal B-cell population can comprise IgA-secreting B cells and/or IgE-secreting B cells.

The polyclonal B-cell population can be obtained by any method known in the art for providing more than one (or at least two) B-cell clones capable of producing IgG antibodies. For example, the polyclonal B-cell population can be isolated or derived from the peripheral blood of a subject. Alternatively, or concomitantly, the polyclonal B-cell population can be isolated or derived from the bone marrow or the spleen. Various methods for obtaining such populations from the peripheral blood have been described and could be successfully applied to the method presented herein. As some of these methods may generate some B cells that do not produce antibodies, it may be necessary to induce the differentiation of B cells into antibody-producing cells. Further, it is also contemplated that IgG-secreting cells within the polyclonal B-cell population be positively selected to enrich for IgG-secreting B cells. Alternatively, or concomitantly, it is also contemplated that IgM- and IgD-secreting cells that may be present in an initial polyclonal B-cell population be negatively selected to enrich the polyclonal B cell population in IgG-secreting B cells. In an embodiment, the polyclonal B-cell population is derived from a mammal, and further, from a human.

The method presented herein enables the production (and the optional recovery/harvest) of a polyclonal IgG preparation. As used herein, the term "polyclonal IgG preparation" refers to a composition comprising at least two IgG antibodies, each recognizing a unique epitope. Epitopes recognized by the antibodies can be located on a single antigen or on different antigens. As indicated above, the present method enables the production of a polyclonal IgG preparation that comprises all the gamma isotypes in relative proportions similar to those encountered in human blood. In an embodiment, the polyclonal IgG preparation comprises at least one the following gamma isotypes: $IgG_1$, $IgG_2$, $IgG_3$ and $IgG_4$. In yet another embodiment, the polyclonal IgG preparation comprises all four gamma isotypes. In an embodiment, the relative proportions of gamma isotypes are similar to those found in normal human blood.

In an embodiment, the polyclonal preparation comprises mostly (or almost exclusively) antibodies of IgG class. In another embodiment, the concentration of IgG in the polyclonal IgG preparation is more than 70%, more than 80%, more than 90%, more than 95% or more than 99% of the total Ig content in the preparation. In still another embodiment, the concentration of IgG in the polyclonal IgG preparation is between 80% and 95%, between 80% and 99% or between 95% and 99%, of the total Ig content in the preparation.

Further, because the method uses a polyclonal B-cell population enriched for IgG-secreting B cells and/or depleted of IgD- and/or IgM-secreting B cells, the resulting polyclonal IgG preparation contains low (or very little) quantities of IgD and/or IgM. As such, in a further embodiment, the concentration of IgM in the polyclonal IgG preparation is less than 10% or less than 5% or less than 1% of the total Ig content of the preparation. In still another embodiment, the concentration of IgM in the polyclonal IgG preparation is between 10% and 5% or between 5% and 1% of the total Ig content of the preparation.

The methods provided herewith improve the production of antibodies during a relatively prolonged culture period. In one embodiment, the concentration of the polyclonal IgG preparation in the culture medium is more than 10 μg/mL, more than 15 μg/mL or more than 20 μg/mL. In yet a further embodiment, the polyclonal B-cell population can be cultured for more than 30 days, more than 40 days, more than 50 days or more than 60 days.

The polyclonal IgG preparation obtained by this method can be used for various purposes. The polyclonal IgG preparation can be used directly as it is generated by the method, or can be further processed prior to its use. For example, the polyclonal IgG preparation can be further fragmented.

In an embodiment, it can be used in imaging techniques. In this particular embodiment, the polyclonal IgG preparation can be coupled (i.e., physically linked) to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive materials include $^{125}I$, $^{131}I$, $^{35}S$ or $^{3}H$. Alternatively, the polyclonal IgG preparation can be coupled to a chemotherapeutic agent; a toxin (e.g., an enzymatically active toxin of bacterial, fungal, plant, or animal origin, or fragments thereof); a radioactive isotope (i.e., a radioconjugate). Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, it can be used for the treatment or prevention of various conditions in which immunoglobulins are administered to alleviate the symptoms of the conditions or prevent the onset of the conditions. Prior to its administration to a patient, the polyclonal IgG preparation can be further isolated or purified. When providing a patient with the polyclonal IgG preparation, the dosage of the administered polyclonal IgG preparation will vary depending upon such factors as the patient's age, weight, height, sex, general medical condition, previous medical history, etc. In general, it is desirable to provide the recipient with a dosage of agent which is in the range of from about 0.1 g/kg to 2 g/kg (patient body weight), although a lower or higher dosage may be administered. The therapeutically effective dose can be lowered by using the present composition in combination with another agent. As used herein, two or more compounds are said to be administered "in combination" with each other when either (1) the physiological effects of each compound, or (2) the serum concentrations of each compound can be measured at the same time. The administration of the polyclonal IgG preparation may be for either a "prophylactic" or "therapeutic" purpose. Polyclonal IgG preparations are administered to the mammal in a pharmaceutically acceptable form and in a therapeutically effective amount. A composition is said to be "pharmacologically acceptable" if its administration can be tolerated by a recipient patient. Such a polyclonal IgG preparation is said to be administered in a "therapeutically effective amount" if the amount administered is physiologically significant. An agent is physiologically significant if its presence results in a detectable change in the physiology of a recipient patient. Polyclonal IgG preparations of the present invention can be formulated according to known methods to prepare pharmaceutically useful compositions, whereby these materials, or their functional derivatives, are combined in admixture with a pharmaceutically acceptable carrier vehicle. Suitable vehicles and their formulations, inclusive of other human proteins, e.g., human serum albumin, are described, for example, in Remington's Pharmaceutical Sciences (16th ed., Osol, A., Ed., Mack, Easton, Pa. (1980)). In order to form a pharmaceutically acceptable composition suitable for effective administration, such compositions will contain an effective amount of one or more polyclonal IgG preparation(s), together with a suitable amount of carrier vehicle. Additional pharmaceutical methods may be employed to control the duration of action. Controlled release preparations may be achieved through the use of polymers to complex or adsorb one or more of the agents of the present invention. The controlled delivery may be exercised by selecting appropriate macromolecules (for example polyesters, polyamino acids, polyvinylpyrrolidone, ethylenevinylacetate, methylcellulose, carboxymethylcellulose, or protamine sulfate) and the concentration of macromolecules as well as the methods of incorporation in order to control release. Another possible method to control the duration of action by controlled release preparations is to incorporate polyclonal IgG preparations into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacrylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (16th ed., Osol, A., Ed., Mack, Easton, Pa. (1980)).

In order to optimize methods presented herein, various steps or parameters can be changed. For example, in an embodiment, the method can further comprise depleting the polyclonal B-cell population from IgM-secreting B cells and/or IgD-secreting B cells. As used herein, the term "depletion" refers to lowering the concentration of IgD- and/or IgM-secreting B cells from the polyclonal B-cell population. This "depletion" (and, consequently, enrichment of IgG-producing B cells) can be performed by any technique known in the art that can negatively select IgD- and/or IgM-secreting B cells. For example, IgD- and/or IgM-secreting B cells can be selected out from an initial polyclonal B-cell population using antibodies specific for IgD- and/or IgM-secreting B cells followed by a negative selection step.

In addition, the method presented herein can also comprise the recovery/harvesting of the polyclonal IgG preparation from the culture medium and/or the cultured polyclonal B-cell population. The recovered/harvested polyclonal IgG preparation can be further purified and/or modified, depending on the intended use for these antibodies.

The culture conditions used in this method should minimize cell death and/or necrosis and favor antibody (e.g. IgG) production. Cells that are submitted to this method are capable of secreting an antibody (preferably an IgG antibody). These cells are either differentiated into antibody-secreting cells or have the ability to differentiate into antibody-secreting cells. The culture medium that can be used in the method described herein can vary and can be determined/formulated by a person skilled in the art to achieve the production of a large quantity of polyclonal IgGs. The culture medium can be a standard medium, such as those currently known and used in the art. The culture medium can contain other additives such as serum, amino acids, antibiotics, vitamins, minerals, buffers, etc. In an embodiment, the culture medium comprises at least one of either interleukin(IL)-4, IL-10 and/or IL-2. In a further embodiment, the culture conditions enable the contact between the polyclonal B-cell population and CD154. In another embodiment, CD154 is provided on a cellular membrane.

The method presently described could also comprise a further step of selecting B cells of interest that produce an antibody specific for a particular antigen or epitope. In this particular embodiment, the B-cell population that has been submitted to the various steps of the method presented herein can be selected based on their ability to produce a specific antibody. Alternatively, antibodies produced by the method can be further selected also based on their ability to recognize a specific antigen or epitope.

In yet another embodiment, because the present method enables the long-term culture of B cells and their multiplication, it can also be used to expand a B-cell population. With this method, the expansion of B cells is at least $10^3$, but it can reach $10^9$. As used herein, the term "expansion" refers to the number of cells at a specified time (at $t_x$) divided by the number of original cells (at $t_0$).

The present invention will be more readily understood by referring to the following examples which are given to illustrate the invention rather than to limit its scope.

Example I

Methodology Used

Peripheral blood B-lymphocyte isolation and cell sorting. Regular blood donors who agreed to participate in this study have signed an informed consent. LRS chambers from Trima Accel™ collection systems (Gambro BCT, Lakewood, USA) containing peripheral blood mononuclear cells were recovered at the end of the apheresis procedure[8]. B cells were isolated from peripheral blood mononuclear cells (PBMC) as previously described[7,8], using the StemSep™ CD19 cocktail (Stem Cell Technologies, Vancouver, Canada). B-cell purity, as determined by flow cytometry, was higher than 95% in all experiments reported herein. Depletion of IgM+ and IgD+ B cells was performed using an EasySep™ custom cocktail specifically targeting IgM and IgD surface molecules (Stem Cell Technologies). After depletion, IgD+ and/or IgM+ cells represented less than 5% of total cells.

Human B-cell culture and exposure to defined culture conditions. Purified B cells were seeded at $0.75 \times 10^5$ to $1.5 \times 10^5$ cells/mL in Primaria™ plates (BD Biosciences, Mississauga, Canada) in the presence of γ-irradiated (75 Gy; 7,500 rad) L4.5 cells expressing CD154[9]. A constant ratio of 3 to 5 B cells per L4.5 cell, which corresponds to about 5000 to 2000 CD154 molecules per B cell as reported previously[6], was used in all assays. B cells were cultured in Iscove's modified Dulbecco's medium (IMDM) supplemented with 10% heat-inactivated Ultra Low IgG™ fetal bovine serum, 5.5 μg/mL transferrin, 6.7 mg/mL sodium selenite, antibiotics (all from Invitrogen, Burlington, Canada), 50 U/mL IL-2, 25 ng/mL IL-10 (PeproTech Inc., Rocky Hill, USA) and 100 U/mL IL-4 (R&D Systems, Minneapolis, USA). L4.5 cells were renewed every 4-5 days, and half of the culture medium was replaced every 2-3 days. Cell counts and viability were evaluated in triplicates by Trypan blue dye exclusion. Generation time ($t_{gen}$) was calculated within the initiation phase of the growth curve according to the formula:

$$\kappa = 1/\ln 2 (\ln[N_{t2}] - \ln[N_{t1}])/t_2 - t_1 \text{ and } t_{gen} = 1/\kappa.$$

Quantification of IgA, IgG and IgM secretion. IgA, IgG, $IgG_1$, $IgG_2$, $IgG_3$ $IgG_4$ and IgM concentrations in culture supernatants were determined by a standard ELISA using sandwich of antibodies specific for the Fc region and whole molecule for each subclass[7]. For the determination of secretion rate in long-term assays, cells were harvested, extensively washed with PBS and seeded at $2 \times 10^6$ cells/mL in IMDM without cytokines and L4.5 cells for 20 to 22 hours, after which culture supernatants were assayed for whole IgG and its subclasses by ELISA.

Analysis of immunoglobulins by isoelectrofocusing. Thin-layer isoelectrofocusing (IEF) was performed on thin-layer 5% acrylamide containing pI 4.6-9.6 ampholytes (Bio Rad Laboratories Inc., Mississauga, Canada). Ten to 20 ng of immunoglobulin samples were focused in three steps, consisting of 100V for 15 minutes, 200V for 15 minutes and 450V for one hour. According to a standard western blot assay, proteins were transferred from gels to nitrocellulose (GE Life Sciences, Piscataway, USA) and membranes were revealed using peroxidase-conjugated goat antibodies specific to human γ chains (Jackson Laboratories, Mississauga, Canada). Detection was done using the ECL™ chemiluminescence kit (GE Life Sciences), following the manufacturer's instructions.

Example II

Long-Term Expansion in Culture of Blood IgG+ B Cells

Figure 1A:
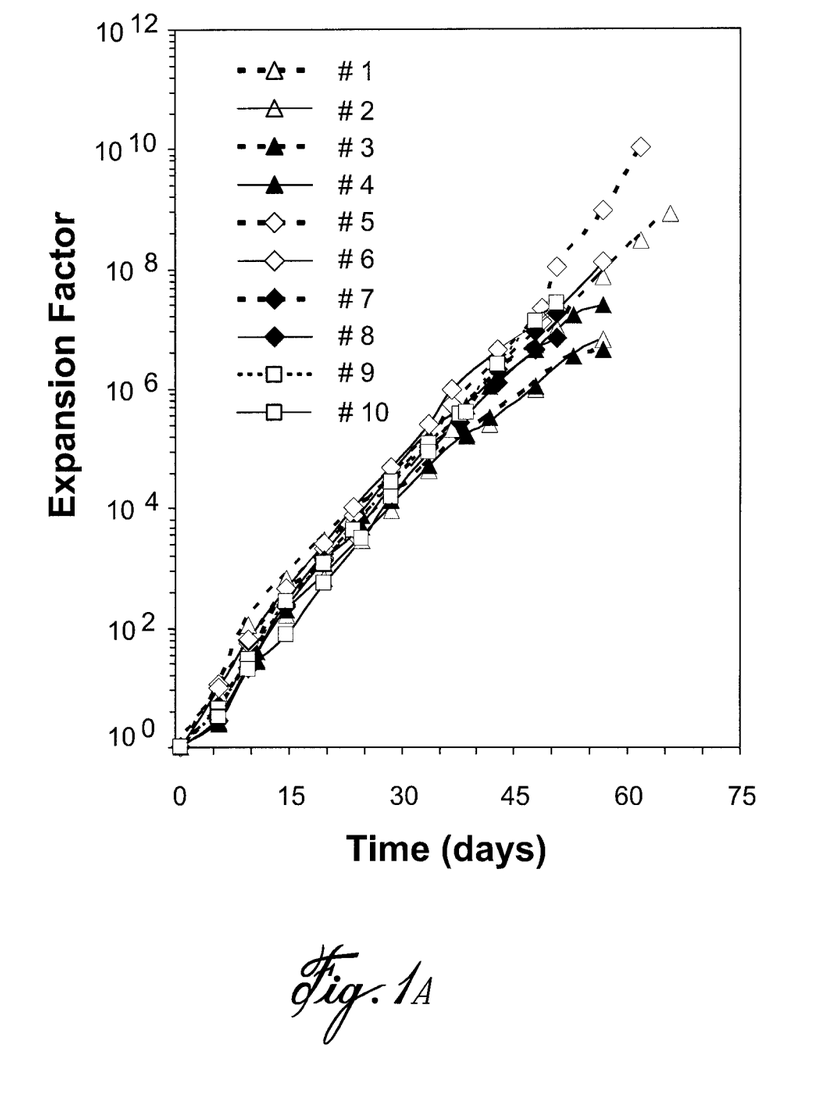
Figure 1B:
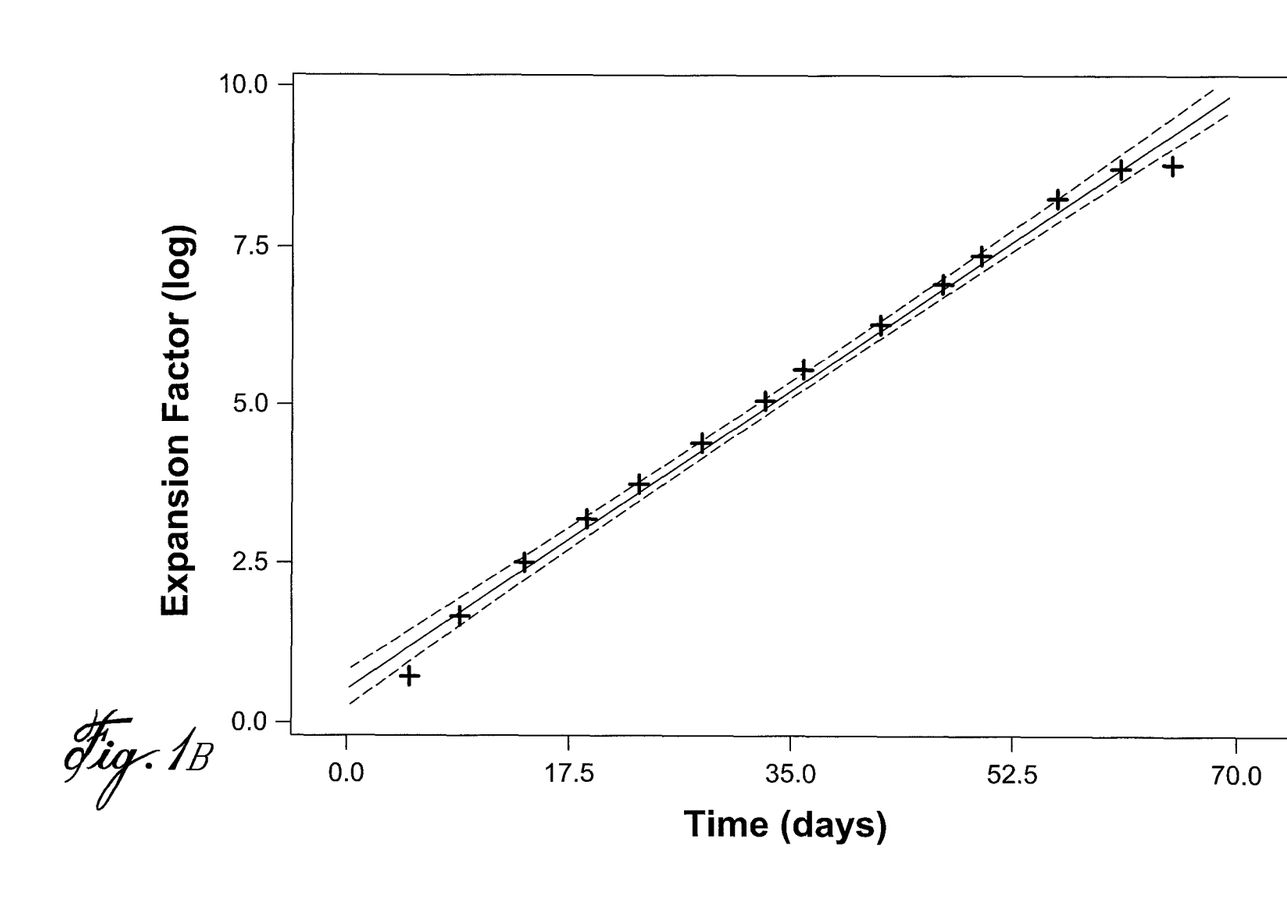
Figure 1C:
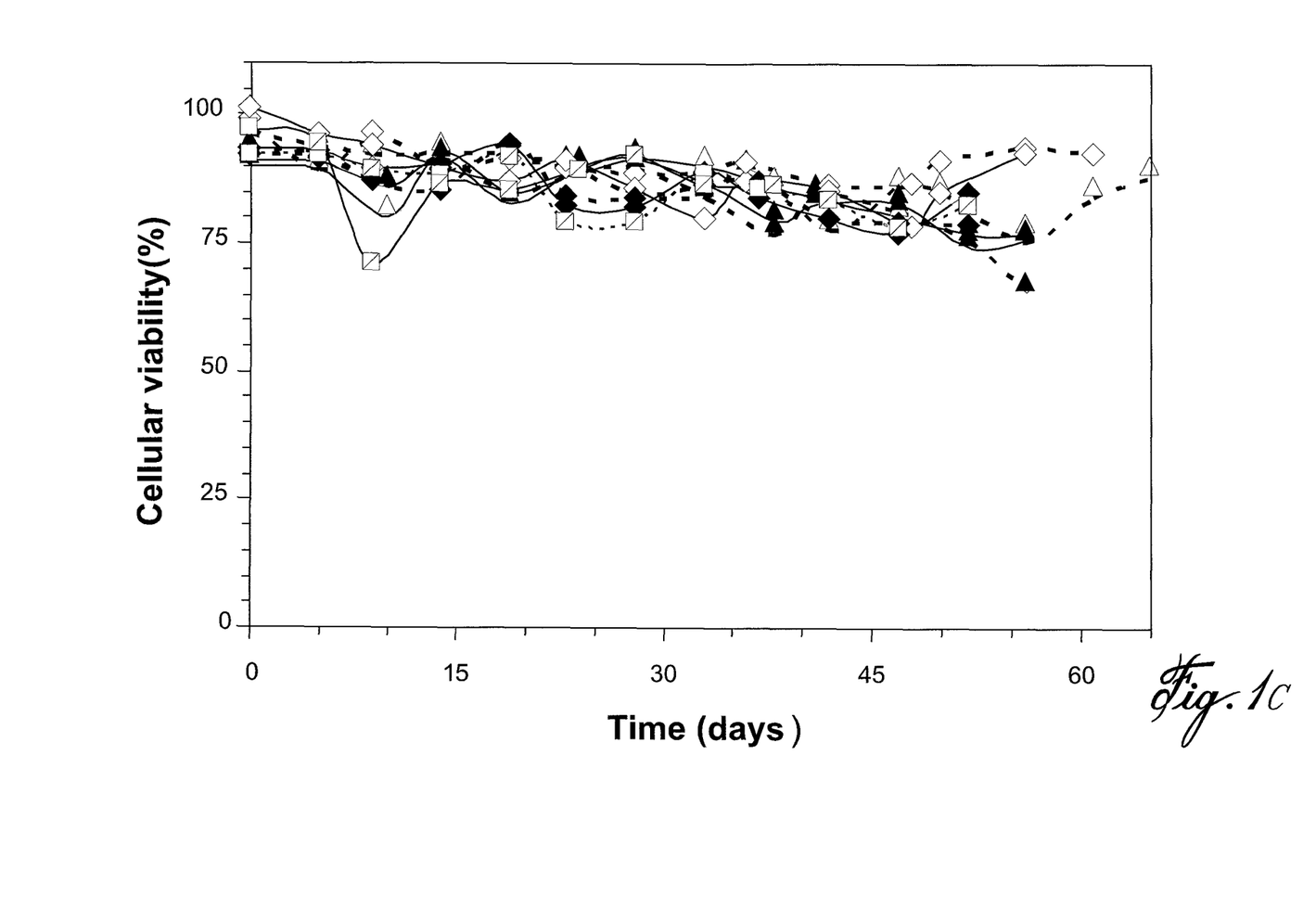
Figure 1D:
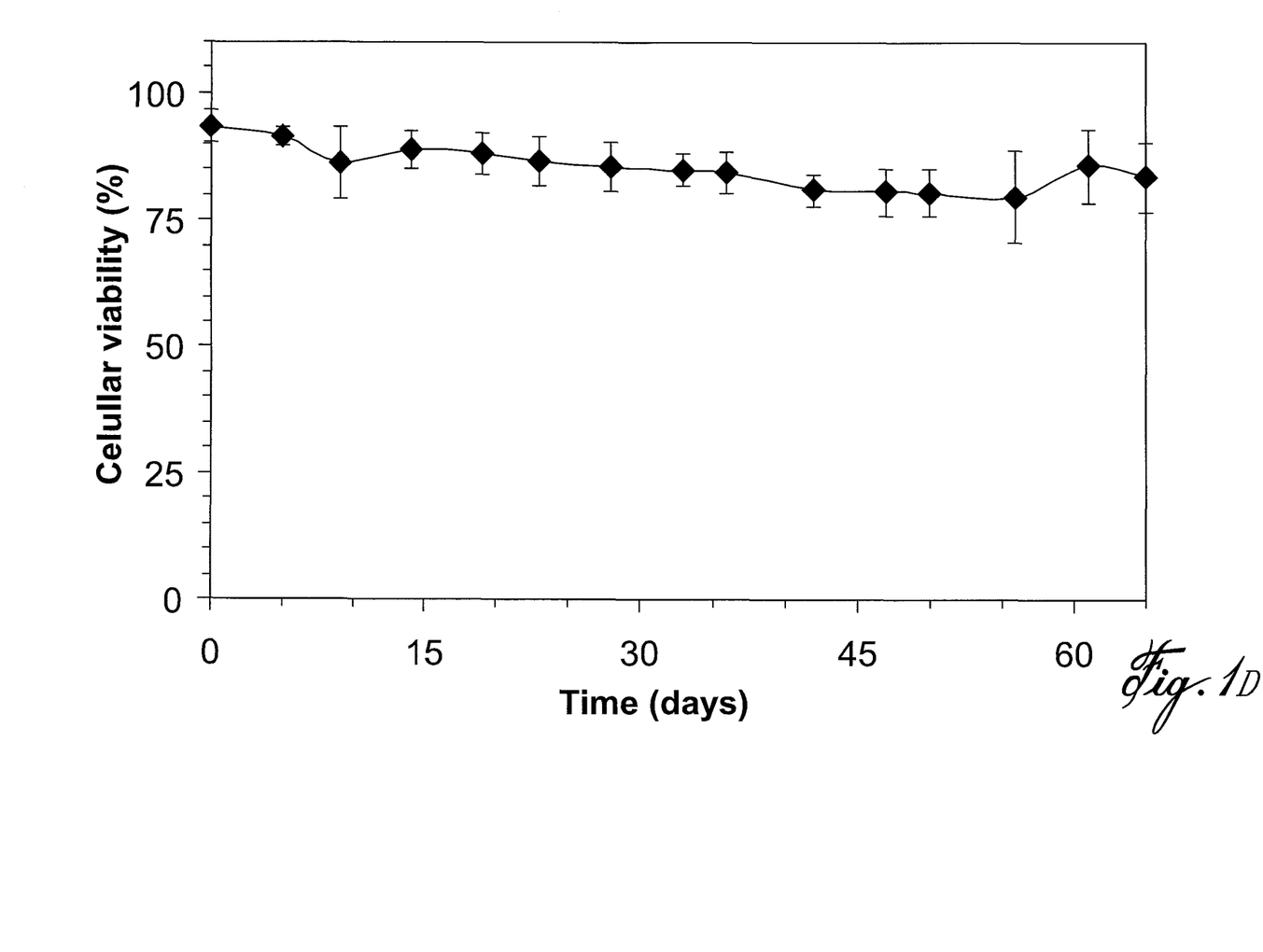

Blood B cells (CD19+) were depleted of IgD+ and IgM+ cells and stimulated in conditions of high CD154 interaction and their proliferation and differentiation were monitored during long-term culture. The results obtained are shown in FIG. 1. Ten independent experiments, corresponding to B cells from ten distinct donors, are presented in FIG. 1A. For all samples, residual IgD+ and IgM+ cells were less than 3% on day 0. During the exponential phase of growth, the mean $T_{gen}$ or doubling time was 44 hours±9 hours. Additionally, expansion rates were remarkably constant in time, and consistent among the ten cultures (FIG. 1B). At the end of the culture period, cell viability was >80% (c.f. FIGS. 1C and D), and the final expansion factor, based on the expansion rate and seeding cell numbers, was ranging from $10^7$ to $10^9$ after 50 to 65 days of culture. During the culture period, the proportion of residual IgD+ cells remained <3%. However, the frequency of IgM+ cells reached about 10%±4% in some experiments.

Figure 3A:
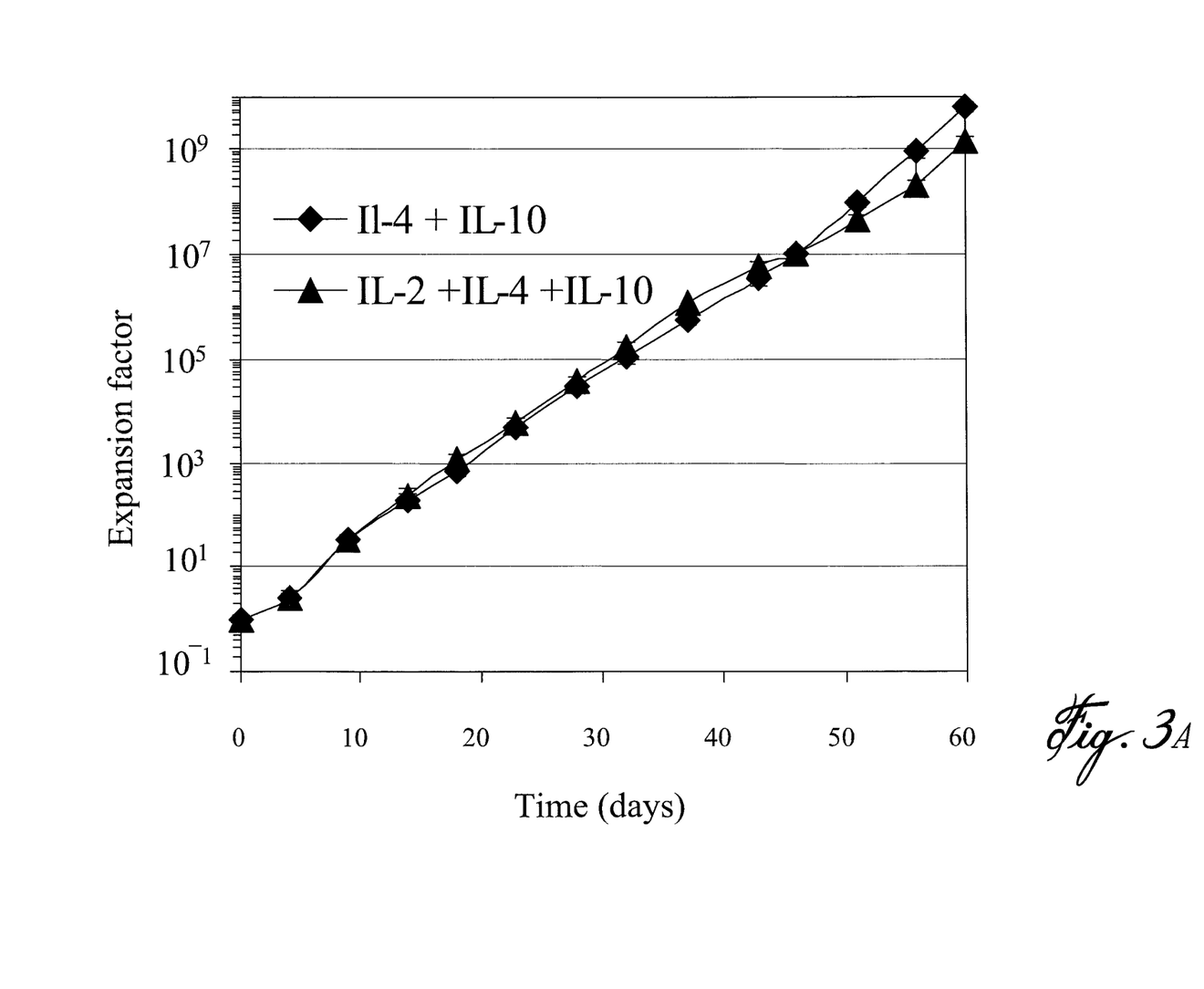

An additional experiment was conducted with another (#11) highly enriched B-cell sample (FIG. 3A) using a mixture of IL-4 and IL-10 in the presence or absence of IL-2. Following negative selection, IgD+ and IgM+ cell frequencies were lower than 0.5%, and remained below 5% and 1%, respectively, over the 60-day culture period. During the exponential phase of growth, the $T_{gen}$ or doubling time reached 33 hours for both tested conditions. At the end of the culture period, cell viability was >90%, and the total expansion, calculated from the expansion rate and seeding cell numbers, was about $10^9$ for both conditions assayed.

Example III

Blood IgG+ B Cells are Highly Efficient at Ig Secretion

Figure 2A:
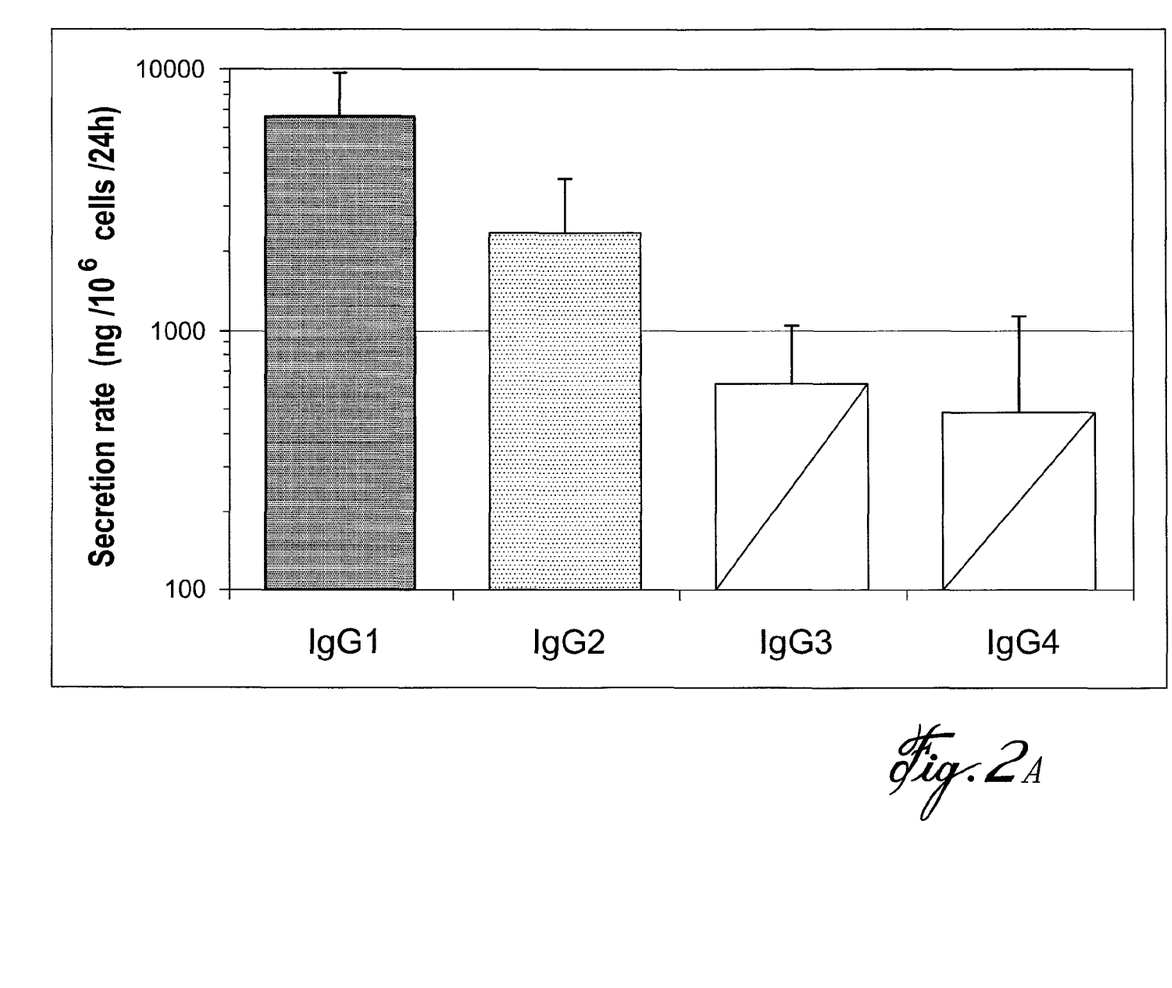
Figure 3B:
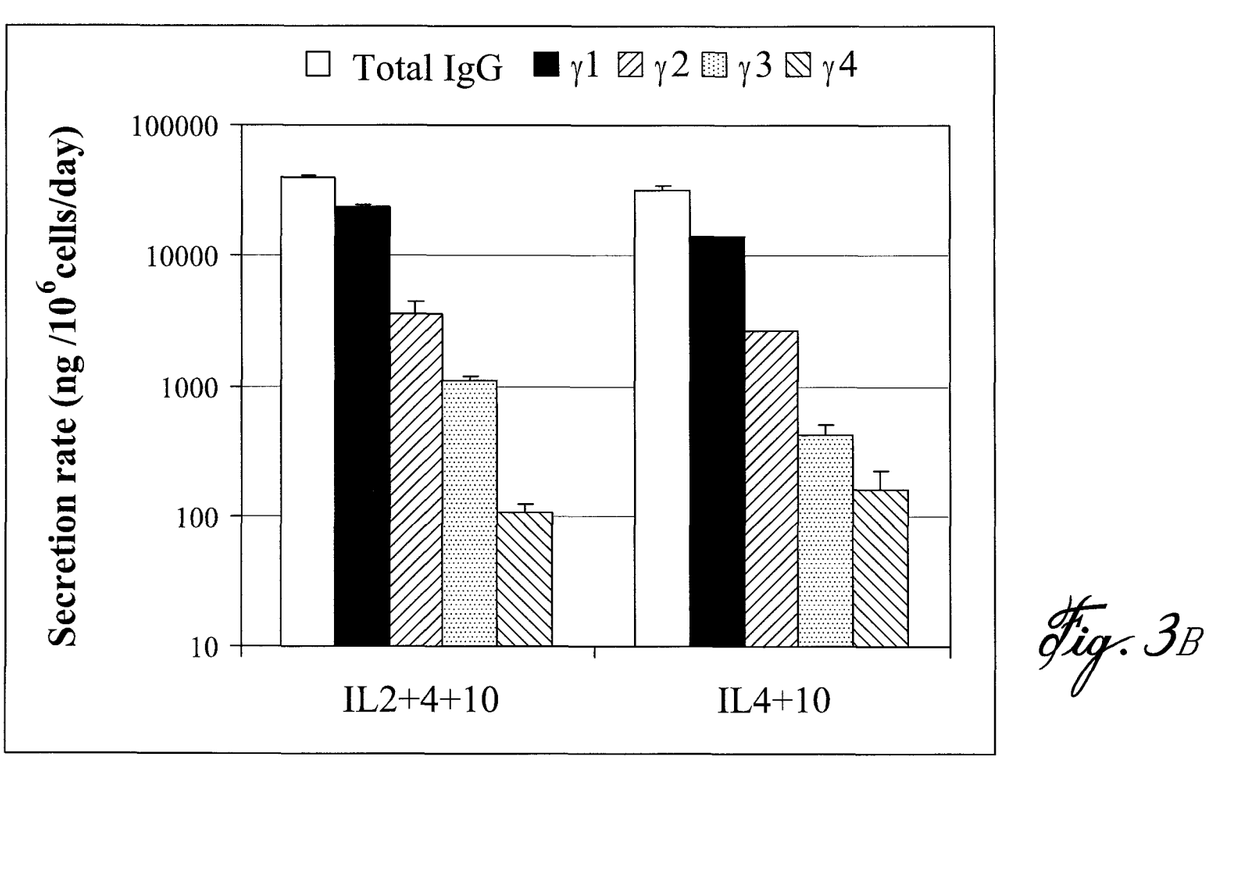

The secretion rate for each IgG isotype was determined in the middle of the culture period, i.e., from day 30 to 37. An average of 30 to 120 μg of total IgG was secreted per $10^6$ cells over a 24-hour period. Interestingly, all gamma isotypes were present in relative proportions similar to those found in human blood, namely $IgG_1 > IgG_2 > IgG_3 > IgG_4$, suggesting that long-term culture of IgG+ human B cells did not induce a bias in the secretion of IgG isotypes (c.f. FIGS. 2A and 3B).

In these assays, IgM secretion rate was ranging from 10 to 1000 ng/$10^6$ cells/day, and was always corresponding to less than 5% of the total Ig content. The IgG concentration in the supernatant of the cell culture previously described in Examples II and III was assayed and the results generated might be an indicator of the capacity of the culture system to produce large quantities of human IgG. The cumulative secretion of the entire B-cell population allowed to reach a concentration of 39 to 89 μg/mL IgG, and again all four gamma isotypes were present in relative proportions similar to those found in human blood.

Figure 2B:
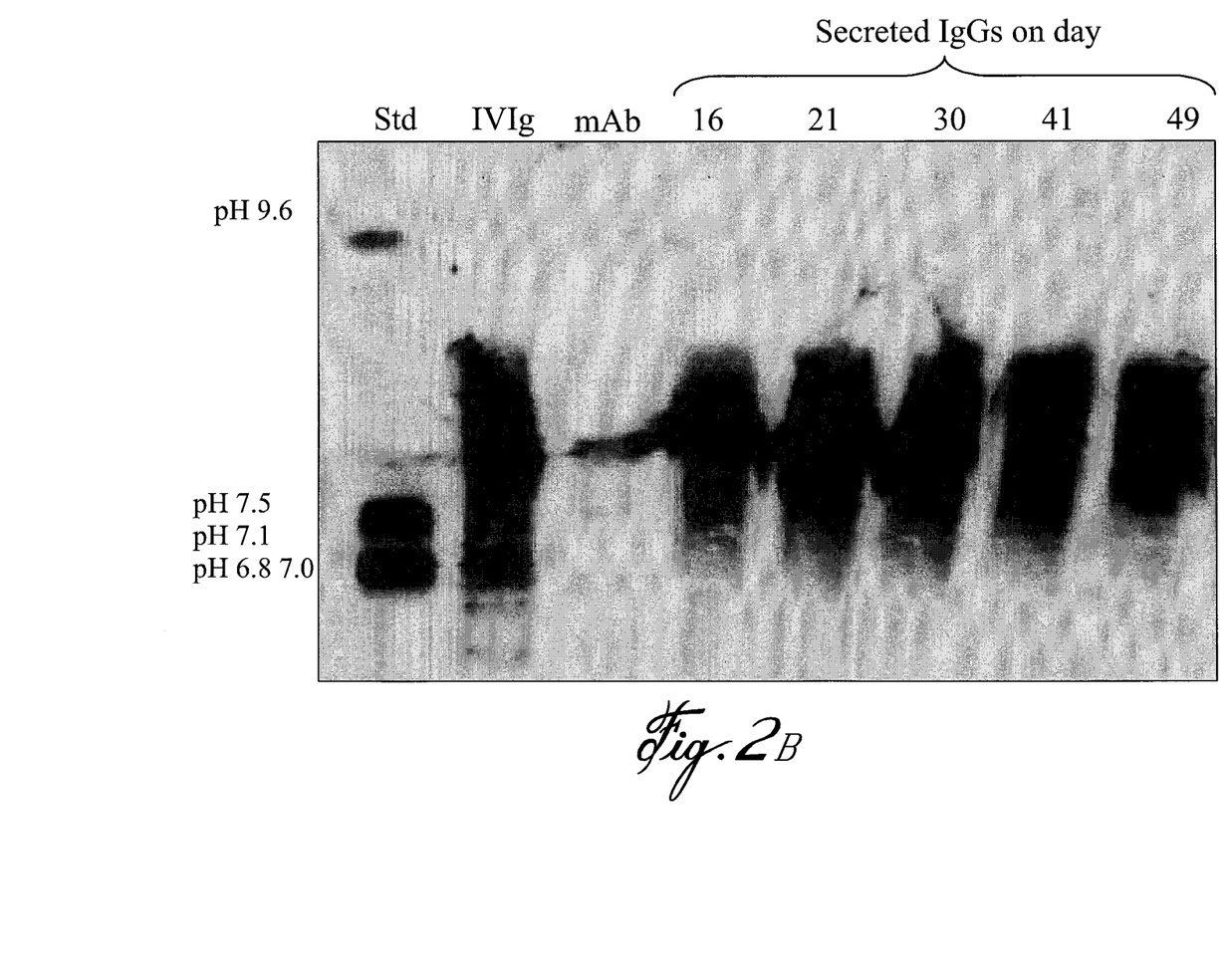

The degree of heterogeneity of secreted IgG molecules was assessed after long-term B-cell culture. More specifically, an experiment was performed to address the issue as to whether IgG produced in these conditions were derived from a limited set of B-cell clones that acquired a growth and/or IgG secretion advantage over time, or else were representative of polyclonal secretion suggesting that a broad, diverse repertoire was maintained over time. As shown in FIG. 2B, the patterns observed following IEF analysis showed smears of protein bands, indicating that the expanded B-cell population maintained its polyclonality, even after long-term culture.

Example IV

Figure 4A:
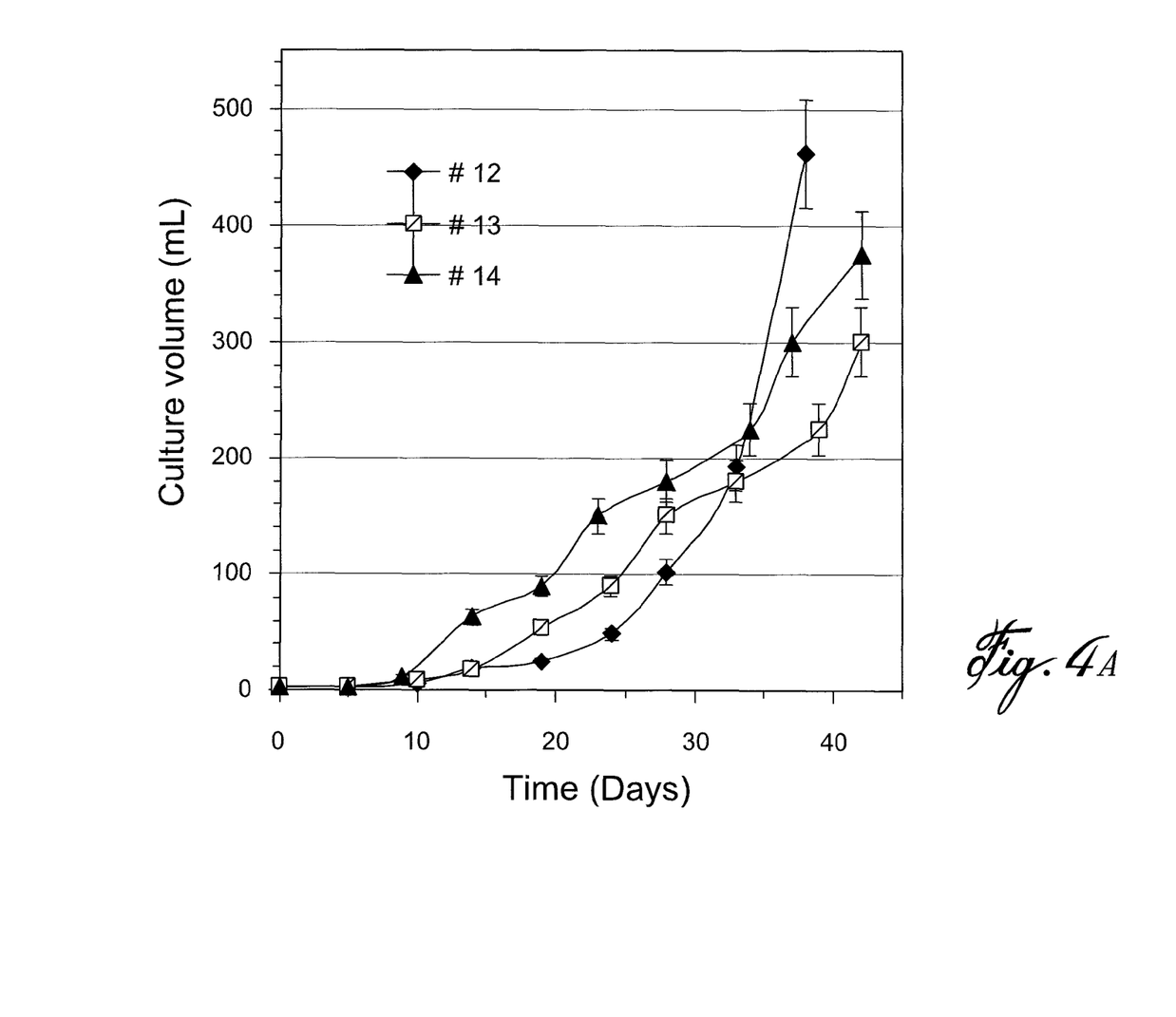
Figure 4B:
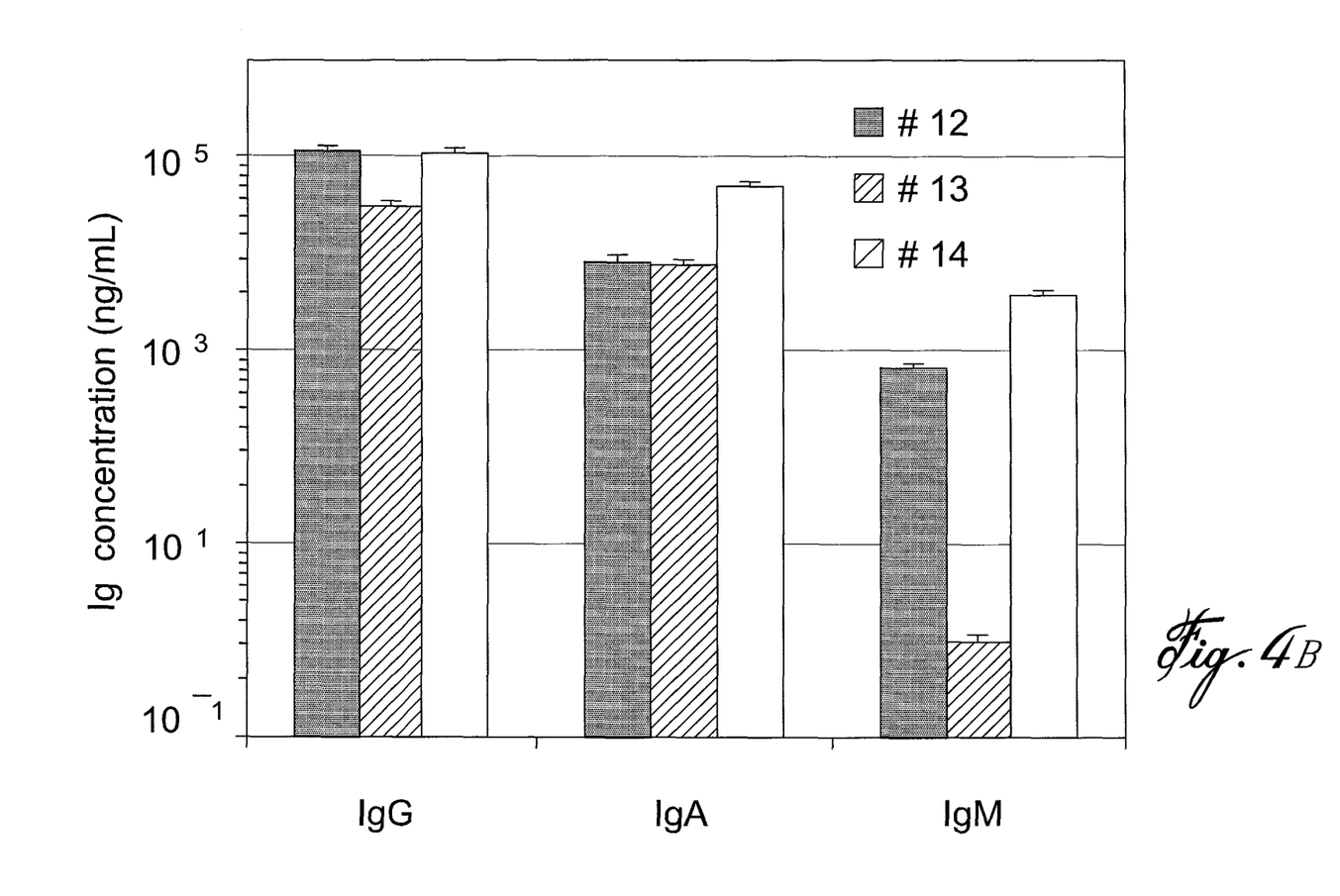

Long-Term Expansion in Culture of Blood IgG+ B Cells in Increasing Culture Volumes The ability of blood IgG+ B cells to expand in larger culture volumes was assessed by serial passaging three long-term cultures in Petri dishes. As shown in FIG. 4A, over a 35- to 40-day period, cultures could be expanded in volumes reaching 300-450 mL. Expansion rates were similar to those obtained with the same blood IgG+ B-cell samples maintained in parallel in 6-well plates Final IgG, IgA, and IgM concentrations (FIG. 4B) and polyclonality evaluated by IEF were similar to those shown in FIGS. 2A, 2B and 3B.

While this invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

REFERENCES

1. Banchereau J., Bazan F., Blanchard D., Briere F., Galizzi J. P., van Kooten C., Liu Y. J., Rousset F. & Saeland S. (1994) The CD40 antigen and its ligand. Annu Rev Immunol, 12, 881.
2. Banchereau J. & Rousset F. (1991) Growing human B lymphocytes in the CD40 system. Nature, 353, 678.
3. Rousset F., Peyrol S., Garcia E., Vezzio N., Andujar M., Grimaud J. A. & Banchereau J. (1995) Long-term cultured CD40-activated B lymphocytes differentiate into plasma cells in response to IL-10 but not IL-4. Int Immunol, 7, 1243.
4. Tangye S. G. & Hodgkin P. D. (2004) Divide and conquer: the importance of cell division in regulating B-cell responses. Immunol, 112, 509.
5. Grammer A. C., Bergman M. C., Miura Y., Fujita K., Davis L. S. & Lipsky P. E. (1995) The CD40 ligand expressed by human B cells costimulates B cell responses. J Immunol, 154, 4996.
6. Néron S., Racine C., Roy A. & Guérin M. (2005) Differential responses of human B-lymphocyte subpopulations to graded levels of CD40-CD154 interaction. Immunol, 116, 454.
7. Fecteau J. F. & Néron S. (2003) CD40 stimulation of human peripheral B lymphocytes: distinct response from naïve and memory cells. J Immunol, 171, 4621.
8. Néron S., Thibault L., Dussault N., Cote G., Ducas E., Pineault N. & Roy A. (2007) Characterization of mononuclear cells remaining in the leukoreduction system chambers of apheresis instruments after routine platelet collection: a new source of viable human blood cells. Transfusion, 47, 1042.
9. Néron S., Pelletier A., Chevrier M. C., Monier G., Lemieux R. & Darveau A. (1996) Induction of LFA-1 independent human B cell proliferation and differentiation by binding of CD40 with its ligand. Immunol Invest, 25, 79.

What is claimed is:

1. An in vitro method for producing a human polyclonal IgG preparation, said method comprising:
 a) obtaining an initial human polyclonal B-cell population;
 b) prior to culture, substantially depleting IgM-secreting cells and IgD-secreting cells from the initial human polyclonal B-cell population so as to obtain a human polyclonal B-cell population enriched in IgG-secreting cells;
 c) placing the human polyclonal B-cell population enriched in IgG secreting cells in a culture medium; and
 d) culturing the human polyclonal B cell population enriched in IgG-secreting cells under conditions enabling the production of the human polyclonal IgG preparation from the polyclonal B cell population;
wherein the human polyclonal B cell population of step b) has a concentration of IgM-secreting cells of less than 5% and a concentration of IgD-secreting cells of less than 5%.

2. The in vitro method of claim 1, wherein the human polyclonal B-cell population of step b) has a concentration of IgG-secreting cells of more than 40%.

3. The in vitro method of claim 1, wherein the human polyclonal B-cell population further comprises IgA-secreting cells.

4. The in vitro method of claim 1, wherein the human polyclonal B-cell population further comprises IgE-secreting cells.

5. The in vitro method of claim 1, wherein the human polyclonal B-cell population is derived from peripheral blood.

6. The in vitro method of claim 1, wherein the human polyclonal IgG preparation comprises at least one of the following gamma isotypes of IgG antibodies: $IgG_1$, $IgG_2$, $IgG_3$ and $IgG_4$.

7. The in vitro method of claim 1, wherein the human polyclonal IgG preparation comprises all the following gamma isotypes of IgG antibodies: $IgG_1$, $IgG_2$, $IgG_3$ and $IgG_4$.

8. The in vitro method of claim 1, wherein the relative proportions of IgG isotypes in the human polyclonal IgG preparation are similar to the relative proportions of IgG isotypes in human blood.

9. The in vitro method of claim 1, wherein the concentration of IgG in the human polyclonal IgG preparation is more than 70% of the total Ig content.

10. The in vitro method of claim 1, wherein the concentration of IgM in the human polyclonal IgG preparation is less than 10% of the total Ig content.

11. The in vitro method of claim 1, wherein the concentration of the human polyclonal IgG preparation in the culture medium supernatant is more than 10 μg/mL.

12. The in vitro method of claim 1, wherein the human polyclonal B-cell population has been cultured for more than 30 days.

13. The in vitro method of claim 1, wherein the IgM secretion rate in the human polyclonal IgG preparation is equal to or less than 1000 ng per $10^6$ B cells per day.

14. The in vitro method of claim 1, said method further comprising harvesting the human polyclonal IgG preparation from the culture medium supernatant.

15. The in vitro method of claim 1, wherein the culture medium comprises at least one of the following: interleukin (IL)-2, IL-4 and IL-10.

16. An in vitro method of expanding a human polyclonal B-cell population, said method comprising:
 a) substantially depleting IgM-secreting cells and IgD-secreting cells from an initial human polyclonal B cell population prior to culture to provide a human polyclonal B-cell population enriched in IgG-secreting cells;
 b) placing the human polyclonal B-cell population enriched in IgG-secreting cells in a culture medium; and
 c) culturing the human polyclonal B-cell population enriched in IgG-secreting cells under conditions enabling the multiplication of the polyclonal B-cell population;
wherein the human polyclonal B-cell population enriched in IgG-secreting cells of step b) has a concentration of IgM-secreting cells of less than 5% and a concentration of IgD-secreting cells of less than 5%.

17. The in vitro method of claim 16, wherein the human polyclonal B-cell population of step b) has a concentration of IgG-secreting cells of more than 40%.

18. The in vitro method of claim 16, wherein the human polyclonal B-cell population further comprises IgA-secreting cells.

19. The in vitro method of claim 16, wherein the human polyclonal B-cell population further comprises IgE-secreting cells.

20. The in vitro method of claim 16, wherein the human polyclonal B-cell population is derived from peripheral blood.

21. The in vitro method of claim 16, wherein the relative proportions of IgG isotype-secreting cells in the human polyclonal IgG B-cell population are similar to the relative proportions of IgG isotype-secreting cells in human blood.

22. The in vitro method of claim 16, wherein the human polyclonal B-cell population has been cultured for more than 30 days.

23. The in vitro method of claim 16, wherein the culture medium comprises at least one of the following: interleukin (IL)-2, IL-4 and IL-10.

* * * * *